(12) United States Patent  (10) Patent No.: US 8,788,009 B2
Greene et al.  (45) Date of Patent: Jul. 22, 2014

(54) HIGH IMPEDANCE SIGNAL DETECTION SYSTEMS AND METHODS FOR USE IN ELECTROCARDIOGRAM DETECTION SYSTEMS

(75) Inventors: Andrew Greene, Leicester, MA (US); Suraj Gorkhali, Spencer, MA (US); Kenneth Burnham, Warren, MA (US)

(73) Assignee: FLEXcon Company, Inc., Spencer, MA (US)

( * ) Notice: Subject to any disclaimer, the term of this patent is extended or adjusted under 35 U.S.C. 154(b) by 484 days.

(21) Appl. No.: 12/505,051

(22) Filed: Jul. 17, 2009

(65) Prior Publication Data

US 2010/0016702 A1 Jan. 21, 2010

Related U.S. Application Data

(60) Provisional application No. 61/081,843, filed on Jul. 18, 2008.

(51) Int. Cl.
*A61B 5/0402* (2006.01)
*H01B 1/00* (2006.01)
*A61B 5/0478* (2006.01)
*A61B 5/04* (2006.01)

(52) U.S. Cl.
USPC ............ 600/372; 252/500; 600/382; 600/393

(58) Field of Classification Search
CPC .. A61B 5/04; A61B 5/0408; A61B 2018/147; A61B 2018/167
USPC .......................... 600/372, 382, 386, 391–393
See application file for complete search history.

(56) References Cited

U.S. PATENT DOCUMENTS

| | | | |
|---|---|---|---|
| 3,911,906 A | | 10/1975 | Reinhold, Jr. |
| 4,008,721 A | | 2/1977 | Burton |
| 4,063,352 A | | 12/1977 | Bevilacqua |
| 4,074,000 A | | 2/1978 | Hankee et al. |
| 4,293,665 A | | 10/1981 | Zalucha et al. |
| 4,352,359 A | | 10/1982 | Larimore et al. |
| 4,353,372 A | * | 10/1982 | Ayer ............................. 600/393 |
| 4,422,461 A | * | 12/1983 | Glumac ........................ 607/152 |
| 4,460,369 A | | 7/1984 | Seymour |

(Continued)

FOREIGN PATENT DOCUMENTS

| | | |
|---|---|---|
| CA | 2477615 | 1/2006 |
| GB | 2115431 | 9/1983 |

(Continued)

OTHER PUBLICATIONS

International Preliminary Report on Patentability for PCT/US2009/020979 filed on Jul. 17, 2009, 9 pages.

(Continued)

*Primary Examiner* — Linda Dvorak
*Assistant Examiner* — Brian M Antiskay
(74) *Attorney, Agent, or Firm* — Gesmer Updegrove LLP

(57) ABSTRACT

A biomedical sensor system is disclosed that includes a high impedance conductive electrode having an electrode impedance of at least about 20 k$\Omega$/sq-mil, and a dielectric material on a first side of the electrode for receiving a discharge of an electrical signal from the dielectric material responsive to the presence of a time varying signal adjacent a second side of the dielectric material that is opposite the first side.

17 Claims, 14 Drawing Sheets

(56) References Cited

U.S. PATENT DOCUMENTS

| | | | |
|---|---|---|---|
| 4,581,821 A | 4/1986 | Cahalan et al. | |
| 4,798,773 A | 1/1989 | Yasukawa et al. | |
| 4,848,353 A | 7/1989 | Engel | |
| 5,120,325 A | 6/1992 | Dow, Jr. | |
| 5,120,422 A | 6/1992 | Liu et al. | |
| 5,143,071 A | 9/1992 | Keusch et al. | |
| 5,338,490 A | 8/1994 | Dietz et al. | |
| 5,362,420 A | 11/1994 | Itoh et al. | |
| 5,388,026 A | 2/1995 | Kanbara et al. | |
| 5,421,982 A | 6/1995 | Ikeda et al. | |
| 5,645,062 A | 7/1997 | Anderson et al. | |
| 5,800,685 A | 9/1998 | Perrault | |
| 6,121,508 A | 9/2000 | Bischof et al. | |
| 6,214,251 B1 | 4/2001 | Wu et al. | |
| 6,232,366 B1 | 5/2001 | Wang et al. | |
| 6,327,487 B1 * | 12/2001 | Stratbucker | 600/382 |
| 6,342,561 B1 | 1/2002 | Engel et al. | |
| 6,576,712 B2 | 6/2003 | Feldstein et al. | |
| 7,076,282 B2 * | 7/2006 | Munro et al. | 600/391 |
| 2002/0037977 A1 | 3/2002 | Feldstein et al. | |
| 2004/0000663 A1 * | 1/2004 | Segall et al. | 252/500 |
| 2004/0073104 A1 | 4/2004 | Brun Del Re et al. | |
| 2004/0210122 A1 | 10/2004 | Sieburg | |
| 2006/0069320 A1 | 3/2006 | Wolff et al. | |
| 2006/0074284 A1 | 4/2006 | Juola et al. | |
| 2007/0010750 A1 | 1/2007 | Ueno et al. | |
| 2008/0208063 A1 | 8/2008 | Brauers et al. | |

FOREIGN PATENT DOCUMENTS

| | | |
|---|---|---|
| WO | WO9531491 | 11/1995 |
| WO | WO9724149 | 7/1997 |
| WO | 2006/131855 A1 | 12/2006 |
| WO | WO 2006131855 | 12/2006 |

OTHER PUBLICATIONS

"A direct comparison of wet, dry and insulating bioelectric recording electrodes," Searle et al. Physiological Measurement, Institute of Physics Publishing, Bristol, GB. vol. 21, No. 2. p. 271-283. May 1, 2000.

International Preliminary Report on Patentability for PCT/US2009/052815 filed on Aug. 6, 2009, 10 pages.

First Chinese Office Action issued by the State Intellectual Property Office of the People's Republic of China on Oct. 10, 2012 in connection with Chinese Patent Appln. No. 200980128654.X, 11 pages.

First Australian Patent Office Examination Report issued on Nov. 3, 2012 in connection with Australian Patent Application No. 2009279710, 4 pages.

Australian Patent Office Examination Report issued on Aug. 27, 2013 in connection with Australian Application No. 2009279710, 2 pages.

Second Office Action issued by the State Intellectual Property Office of the People's Republic of China and English translation thereof, issued on Jun. 27, 2013 in connection with Chinese Application No. 200980128654.X, 6 pages.

English Translation of the Japanese Office Action issued on Nov. 19, 2013 in connection with Japanese Application No. 2011-518934 filed on Jul. 17, 2009.

* cited by examiner

HIGH IMPEDANCE SIGNAL DETECTION SYSTEMS AND METHODS FOR USE IN ELECTROCARDIOGRAM DETECTION SYSTEMS

PRIORITY

The present application claims priority to U.S. Provisional Patent Application Ser. No. 61/081,843 filed Jul. 18, 2008, the disclosure of which is hereby incorporated in its entirety.

BACKGROUND OF THE INVENTION

The invention generally relates to sensor systems for detecting electrical signals within subjects, and relates in particular to electrocardiogram detection systems.

Conventional electrocardiogram (ECG) systems generally include an electrically conductive material that provides a conductive path between a surface of a subject and medical instrumentation. Sensors for use in biomedical applications such as ECG applications, are disclosed for example, in U.S. Pat. No. 4,848,353, which discloses an electrically-conductive, pressure sensitive adhesive; U.S. Pat. No. 5,800,685, which discloses an electrically conductive adhesive hydrogel; and U.S. Pat. No. 6,121,508, which discloses a conductive hydrophilic pressure sensitive adhesive.

FIG. 1, for example, diagrammatically shows a conductive sensor device 10 of the prior art that includes an ionically conductive adhesive 12, a conductive electrode 14, and a supporting substrate 16. The ionically conductive adhesive 12 is applied to a patient, and electrical signals within the patient underlying the adhesive 12 travel through the adhesive 12 to the conductive electrode 14, which is electrically coupled to monitoring equipment. Certain ECG systems, for example, employ an ionically conductive hydrogel that includes water soluble salts dispersed therein, and in certain systems, these hydrogels are formulated to also function as the skin attachment adhesive.

Such hydrogels typically contain some amount of water within a gel and require that the material be maintained in a sealed environment (e.g., in sealed packages) until being used. Such materials are generally not re-usable in environments where the humidity is not closely controlled. These limitations adversely affect both the cost of sensors that use such conductive adhesives as well as the amount of use that any particular sensor may enjoy.

The hydrogels perform as signal receptors via an ionically conductive mechanism and are therefore low impedance receptors. For example, the conductive electrode may include silver and silver chloride (Ag/AgCl), which typically has a sheet resistance of between 0.1 and 0.5 Ohms/sq-mil. The units Ohms/sq/mil are conventionally used to refer to surface resistivity (Ohms/square) over a volume, yielding Ohms/sq-mil. The conductive layer is deposited over a conductive carbon coated polymeric film (typically having an impedance range of between 1-1000 Ohms/sq/mil) and a conductive lead that is used to couple the electrode to monitoring equipment. The electrode layer serves as a transducer between the ionically generated biological signal and the electrical signal transmitted in the conducting solution. The chloride serves as the ion in the electrolyte. Current flows freely across the electrode because the Ag/AgCl chemical structures are stable.

When the hydrogel of an electrode is placed in contact with the skin, ions will diffuse into and out of the metal via the hydrogel. Copper has an electrode potential of 340 mV, which is a greater potential than exists in an ECG signal (~1 mV). The reference electrode should therefore, cancel this potential, but in practice this is not the case. Electrode potentials change with time due to the ionic interaction. Also, any two electrodes and the underlying skin surfaces are not identical. For these reasons the electrode potentials differ. The electrode potentials appear as signal offset. Silver chloride (AgCl) has a potential of under 5 mV, which is easily handled by typical monitoring technology and will not interfere with the ECG signal. For this reason the AgCl produces low levels of noise (less than 10 µV) which is ideal for the ECG application since the amplitude of the heart palpitations that are required to be transmitted to the monitoring equipment.

The number of signal detecting devices used in a harness system may typically range from 3 to 13 electrodes or more. Employing a larger number of detection points provides that many points of reference are available for monitoring a subject, such as a patient's heart. As shown in FIG. 2, some ECG harness systems provide ten or more receptors (electrical contacts) 20 that are coupled to a common harness 22 that leads to an ECG device (not shown) via a connector 24. Harness systems such as shown in FIG. 2 may be easier to hook-up to the ECG monitor than separately-wired sensors, and may be more comfortable for the patient as well as more securely attachable to the patient. Because the hydrogels are low impedance therefore, the ECG harness systems must also be low in electrical impedance.

U.S. Patent Application Publication No. 2004/0000663 discloses a water insensitive alternating current responsive composite that may be used as an adhesive or a polymeric film in a sensor, and provides that an alternating current signal on one side of the composite may be capacitively coupled to the other side of the composite by having the dielectric properties of the material change with the application of an alternating current field (e.g., exhibits dielectric dispersion) such that a charge is released from the composite at the other side of the composite responsive to the changing dielectric properties. The signal receptive materials of U.S. Patent Application Publication No. 2004/0000663 are disclosed to have impedance values of about 100 kΩ or higher.

There remains a need, however, for inexpensive yet effective biomedical sensor harness and wiring systems that may be easily and economically employed in a variety of applications, and that provide improved sensitivity and useful information to a wide variety of medical personnel.

SUMMARY

In accordance with an embodiment, the invention provides a biomedical sensor system that includes a high impedance conductive electrode having an electrode impedance of at least about 20 kΩ/sq-mil, and a dielectric material on a first side of the electrode for receiving a discharge of an electrical signal from the dielectric material responsive to the presence of a time varying signal adjacent a second side of the dielectric material that is opposite the first side.

In accordance with a further embodiment, the invention provides a method of detecting a time varying signal from a patient. The method includes the steps of: receiving the time varying signal from a patient; changing dielectric properties of a dielectric material responsive to the time varying signal from the patient; providing an output signal to a conductive electrode of a biomedical sensor; and providing the output signal to a monitor system via a signal path that has a resistance of at least about 1 Ω/sq-mil.

In accordance with yet a further embodiment, the invention provides a biomedical sensor system that includes a first conductive electrode and a second conductive electrode. The first and second conductive electrodes are provided in contact with a signal receptive material that is contiguous with both the first conductive electrode and the second conductive electrode.

BRIEF DESCRIPTION OF THE DRAWING

The following description may be further understood with reference to the accompanying drawings in which.

Figure 1:
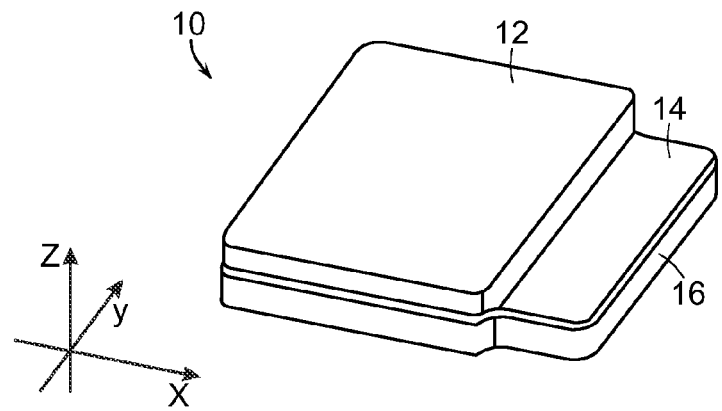
FIG. 1 shows an illustrative diagrammatic view of a biomedical sensor of the prior art.
Figure 2:
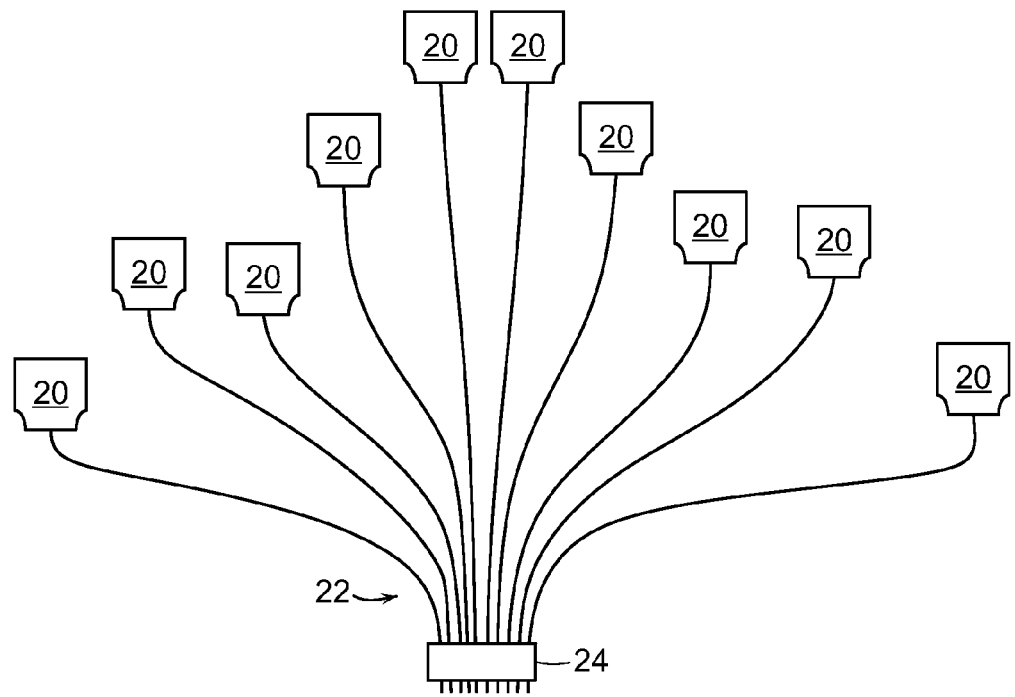
FIG. 2 shows an illustrative diagrammatic view of a biomedical sensor harness system of the prior art.

The drawings are shown for illustrative purposes and are not to scale.

DETAILED DESCRIPTION

It has been discovered that a high impedance continuous signal receptive material may be provided in accordance with the invention that may serve as a common attachment adhesive for multiple high impedance electrodes, for example, covering an array of sites, and further that an inexpensive high impedance connection system may be used with the multiple high impedance electrodes. The signal receptive material (SRM) is a high impedance (e.g., greater than 20 kΩ/sq.-mil) material that is responsive to a localized time varying signal, yet does not permit ionic conductivity throughout the material. Many advantages may be provided by such a system. A first of such advantages is simplicity of manufacturing. It is not necessary to register (align) the SRM to the individual electrodes. Instead, multiple electrodes may be placed on a common SRM. An additional benefit is that the increased adhesive area may allow for an optimal bond to the patient. The use of high impedance electrodes (e.g., greater than 50 kΩ/sq.-mil), and connection systems (e.g., greater than 50 kΩ/sq.-mil) also facilitate reducing the overall system cost and complexity of the electrodes. A flexible substrate could also be used as a supporting structure, and such a supporting substrate could be conformable and water vapor and oxygen permeable. Such substrate materials are commonly found for example, in medical applications for use in wound dressings and surgical drapes.

As mentioned above, a technical problem that prevents conductive composites such as hydrogel adhesives from being used in such a way is the fact that the hydrogels have low impedance along the X, Y, and Z dimensions. Thus, if such an adhesive were to span across two or more conductive electrode sensors, any signal generated at one site might be conveyed over the mass of the hydrogel, thus losing the signal specificity to a particular site. For a material to function properly in such an application it would have to have high internal impedance yet still be capable of detecting a biomedical signal and conveying some representative signal to the site specific electrodes.

In accordance with the invention, a high impedance sensor is employed, such as a sensor that is dielectric yet changes its dielectric properties in the presence of biomedical signals, which are typically time varying signals such as alternating current signals. Such a sensor may include a polymeric material and a polar material that is substantially dispersed within the polymeric material as disclosed, for example, in U.S. Patent Application Publication No. 2004/0000663, the disclosure of which is hereby incorporated by reference in its entirety. Using the testing protocol that is described therein, such an adhesive may be provided. An example of such a polymeric material with a polar material substantially dispersed within the polymeric material is, for example, the EXH 585 adhesive product as sold by FLEXcon Company, Inc. of Spencer, Mass. This adhesive exhibits resistance values of about 200,000 Ohms. By comparison, hydrogels exhibit resistance values of less than 3,000 Ohms (for an individual electrode pair) as required by the American National Standards Institute and the Association for the Advancement of Medical Instrumentation (ANSI/AAMI) in accordance with standard EC12 for disposable ECG electrodes. Conventional hydrogels, in fact, must be more conductive than a patient's skin in order to function properly.

Utilizing the selection methods stated within U.S. Patent Application Publication No. 2004/0000663 for compatibility, organo-salts may be provided within the continuous polymeric medium. Non-tacky variants may also be formulated to have the same capacitive coupling, and thus signal responsive characteristics, as thermally activated adhesive systems. Non-pressure sensitive adhesive (non-PSA) variants may have desirable characteristics in some sensing applications, where the adhesion properties may not be needed or be desirable, such as, for example, a sensor array where the test subject is placed on top of the array and there is little to no movement of the test subject during the test.

To determine the impedance of a conventional hydrogel and for a sample of the above mentioned EXH 585 product, an HP 33120A Waveform Generator (as sold by Hewlett Packard Company of Palo Alto, Calif.), creating a 10 Hz sinusoidal waveform signal was used. This signal was then passed through a test sample meeting the ANSI/AAMI EC-12 specification, adhesive to adhesive configuration for tab electrodes. The response signal was received by a BK Precision 100 MHz Oscilloscope model 2190 as sold by B&K Precision Corporation of Yorba Linda, Calif. The resulting waveform display was compared to those produced from tests of various known resistances until an equivalent matching waveform was obtained. The known resistance value that produced the waveform exhibiting the best match to the test sample was then taken as the equivalent matching resistance value for that test sample.

The present invention provides that a contiguous high impedance signal receptive material (SRM) may be used that has many signal detection sites, and further that a high impedance connection system may be employed. Again, some advantages of such a system include ease of application to the patient, better total adhesion to the patient due to greater total bonding area, significantly less a chance of any single electrode coming loose, and the opportunity for using multiple site positions, whether or not in a defined combination, to yield a more accurate profile of, for example, the electrical activity of a patient's heart.

Another advantage in using high impedance SRM that does not use an ionic conductive mechanism to conduct biomedical signals is that it allows a lower cost conductive structure to be used for signal transmission. The need for a silver/silver chloride contact electrode is avoided and lower cost contacts such as vacuum deposited aluminum or a conductive carbon coating, or for that matter most conductive contact materials would be fully functional for use with the SRM.

Figure 3A:
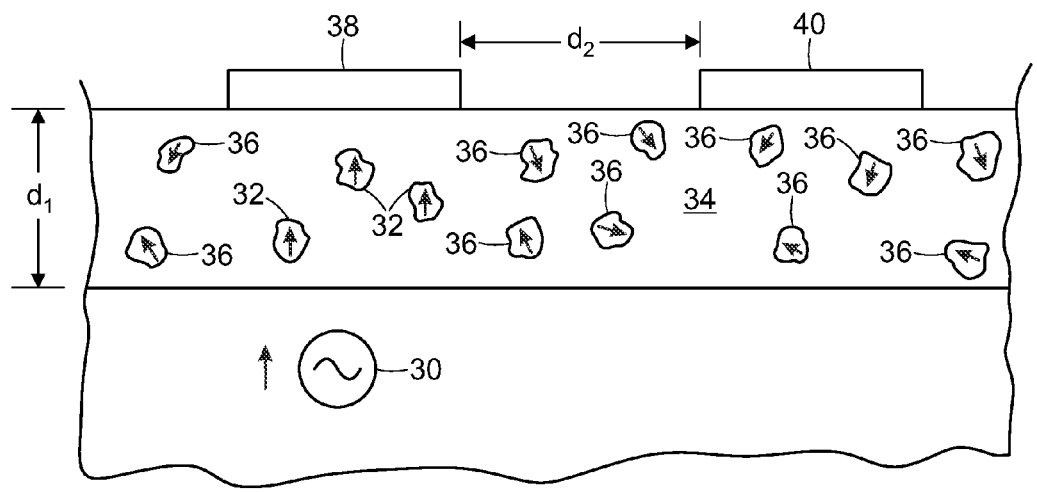
FIGS. 3A and 3b show illustrative diagrammatic views of a sensor system in accordance with an embodiment of the invention during use.
Figure 3B:
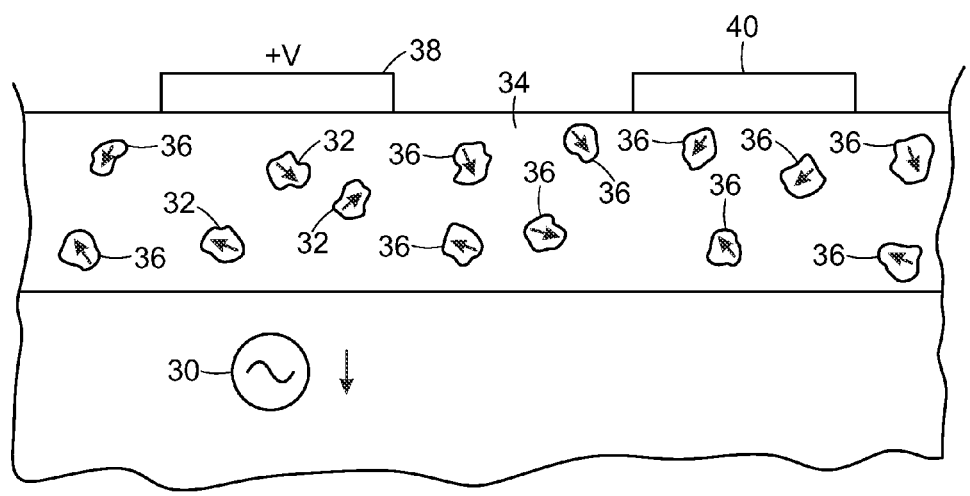

FIGS. 3A and 3B show illustrative views of a signal receptive material of the invention in which a biomedical signal (e.g., a time varying signal such as an alternating current signal) within a subject, such as a patient's heart, is represented at 30. In FIG. 3A, the biomedical signal at 30 is rising in amplitude, and in FIG. 3B, the biomedical signal at 30 is falling in amplitude.

When the biomedical signal 30 rises in amplitude, polar material 32 dispersed within a polymer 34 that is between the biomedical signal at the surface of the subject and a high impedance electrode 38 becomes aligned with the biomedical signal, while polar material 36 that is not immediately adjacent to the biomedical signal and the high impedance electrode 38 does not become aligned. In particular, when the polar material 32 becomes aligned as shown in FIG. 3A, the dielectric properties of the polymer matrix 34 in the area of the aligned polar material 32 change.

As shown in FIG. 3B, when the biomedical signal falls in amplitude, a small signal is discharged from the area of the formerly aligned polar material 32 due to the relaxation of polarization of the dielectric material. This small signal is passed by a high impedance conductor 38 to a detection circuit. If another high impedance conductor 40 is nearby the high impedance conductor 38, it will not receive a charge because the polar material near the high impedance conductor 40 does not align responsive to the signal 30. In this way, high impedance conductors may be placed very close to one another without mutual interference. For example, one may specify that the distance between high impedance conductors 38 and 40 ($d_2$ as shown) should be at least as large as the thickness ($d_1$) of the polymer matrix that includes the polar material.

In this way, a representative output signal is generated that is representative of the original biomedical signal at a specific site. The representative output signal is generated responsive to changes in the dielectric properties of the composite material (the SRM), and the dielectric properties are changed responsive to the presence of a time varying signal from within the subject. Because the SRM is not conductive, but is instead a dielectric, multiple sensor conductors may be placed near each other on a continuous SRM. The SRM, therefore, exhibits dielectric dispersion in a subset area of the SRM rather than over the entire SRM responsive to a signal that is local to the subset area.

Figure 5:
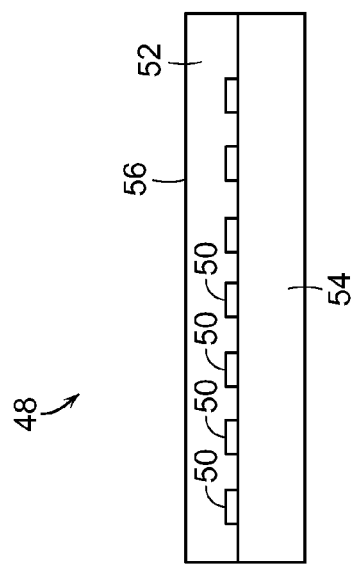
FIG. 5 shows an illustrative diagrammatic side view of the sensor system of FIG. 4.
Figure 4:
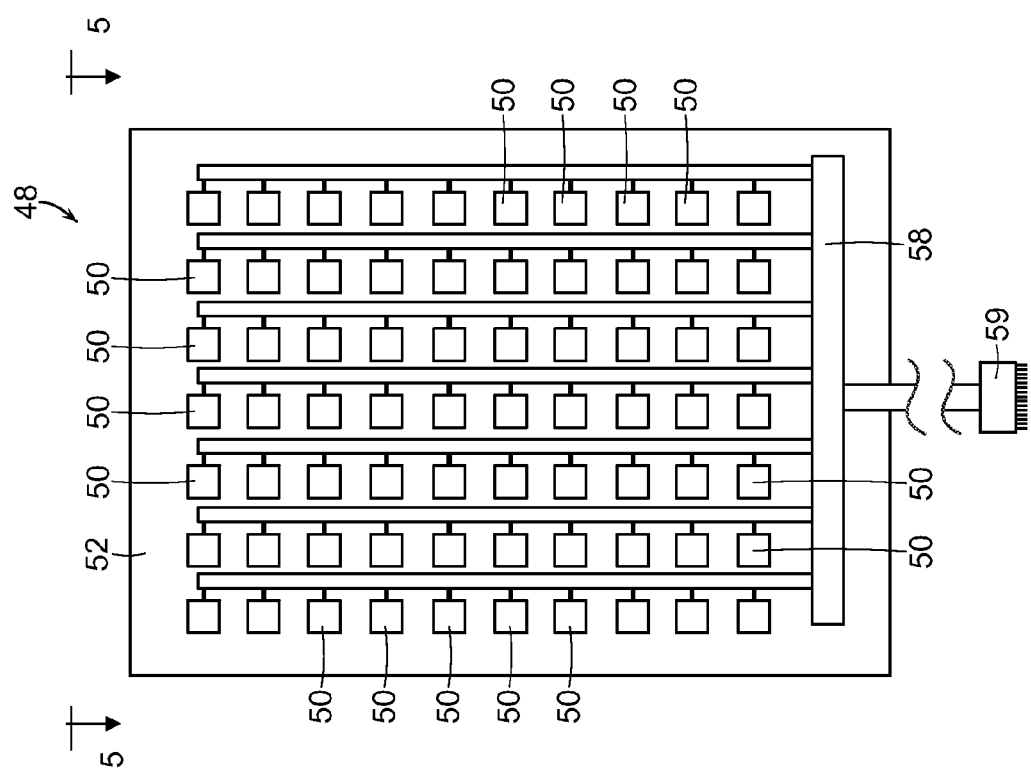
FIG. 4 shows an illustrative diagrammatic plan view of a sensor system in accordance with an embodiment of the invention that includes an electrode array.

FIGS. 4 and 5 a multi-site sensing array 48 that may be provided using a high impedance SRM in accordance with an embodiment of the invention in which an array of high impedance electrodes 50 is provided on a continuous SRM material 52 as described above. FIG. 4 shows a top view through a transparent SRM material 52, and FIG. 5 shows a side view thereof taken along line 5-5 of FIG. 4. Such an array may be used in applications such as ECG monitoring as well as a wide variety of other medical and non-medical applications. As also shown in FIG. 4, the high impedance electrodes and SRM composite may be supported by a releasable support substrate or carrier 54 that is separated from the SRM 52 and high impedance electrodes 50 following application of the exposed surface 56 of the SRM to a patient.

While FIGS. 4 and 5 show a multi-Sensor Pad array, other layouts may also be provided. Data received from such a dense array of sensors may be provided for example, at a connector 69 using collection bus 58 fed by auxiliary buses or by a conventional multiplexing method. The selection of which of the sensing pads are active may be programmed in, or may be determined automatically by an algorithm or other method of information processing analysis, even after the array is applied. The active pad configuration could be changed anytime during the monitoring cycle. Thus the signal receptors may be selectively chosen in order to provide the diagnostician with the optimal viewing angle for a specific palpitation. Viewing angle accuracy and control through this vector method is greatly improved. The possibility of a shorted or improperly connected receptor contaminating an accurate measurement would be greatly reduced.

The choice of the SRM, such as discussed above or any other similar SRM is based on two fundamental properties: 1) High impedance, such as for example, impedance greater than 200,000 Ohms measured as per American National Standard for Pregelled ECG Disposable Electrodes (ANSI/AAMI EC12); and 2) That the mechanism of signal transfer is not a function of ionic conductivity. This enables having, for example, a single SRM layer and multiple sensing pads leading to multiple conductive pathways, without having the signals interfere with one another. Capacitive coupling needs a conductive layer (other than a patient's body for example) to complete a capacitive structure, thus allowing for the option of having the SRM layer continuously extending across more than one sensing pad. This is not possible with low impedance, ionically conductive hydrogels.

For thin high impedance conductive coatings, such as printed lead wires or printed high impedance electrodes, surface resistivity characterizes the impedance. As discussed above, the surface resistivity of materials is reported in units of Ω/square area. The square is a dimensionless unit representing an area equal to the square of the width of the thin coating ($W^2$). Typically those skilled in the art normalize this value to a coating with a thickness of 1 mil (0.001 inches), resulting in unit of Ω/sq-mil (Ohms per square per mil). Knowledge of a material's surface resistivity allows the calculation of the resistance for a given thin deposit of that material. For example:

| | |
|---|---|
| $R_s =$ | surface resistivity in Ω/sq |
| $R_v =$ | volume resistivity in Ω/sq-mil |
| $T =$ | coating thickness in mils |
| $L =$ | length in mils |
| $W =$ | width in mils |
| $R =$ | $R_s \times (L/W) \times (1/T)$ |

The use of the high impedance SRM in the area of biomedical monitoring has several advantages. First, the high impedance electrode may be composed of lower cost materials rather than materials including costly silver/silver chloride. Further the use of non-metallic higher impedance conductors, to form the high impedance output contacts leading to the ECG monitor, would be acceptable. High impedance materials such as, but not limited to, a conductive carbon coating product from FLEXcon such as their EXV-216, or intrinsically conductive polymers such as the CLEVIOS family of products sold by H.C. Stark GmbH of Germany, or carbon nanotube dispersions such as Super HiPCO nanotubes available from Carbon Nanotechnologies, Incorporated of Houston, Tex., could be substituted for the silver/silver chloride electrode of the prior art. Both the high impedance electrodes and the high impedance output contacts may be printed on a common supporting substrate. Further cost savings may be obtained from the ease of manufacturing as well as reduced thickness of the SRM.

Because multiple high impedance electrodes may be placed on a continuous SRM, registration to a specific electrode is not as critical as is the case with an ionically conductive hydrogel, which may reduce manufacturing costs. Also, the thickness of an SRM which operates through capacitive coupling may be less than that of an ionic electrolyte (e.g., hydrogel), which is often 300-625 microns thick. This extra hydrogel mass helps ensure a gap free skin contact, as well the ability to pick up the signals from the heart. In contrast, the intrinsic adhesion of the capacitively coupled SRM is more a function of the polymer base chosen. Thus adhesion may be better tailored to the needs of the application and the signal pickup is not a function of adhesive mass. The thickness of the SRM may, therefore, be for example between about 5 microns and about 200 microns. This provides, that the resulting biomedical sensor device (including a high impedance conductor, a dielectric material and an optional support material) may have a total thickness of less than about 250 microns, which is less than the thickness of a conventional hydrogel alone.

In fact there are advantages with respect to improved defibrillation overload recovery performance when using a thinner layer of the SRM (preferably 25-100 microns), consistent with maintaining adequate contact to the patient's skin. Thinner layers of the SRM would, of course, have cost advantages. These advantages would still be maintained even over a wider bonding area. The cost reduction motive has lead to the use of less and less contact area to save on the hydrogel and the silver/silver chloride cost. Using a capacitively coupled SRM, at a thinner, 5-200 microns deposition, even over a greater surface area, would still maintain a significant material and manufacturing cost advantage. Beside the economic advantage of using a low deposition of the signal receptive material, using a thinner signal receptive material provides for a greater anisotropic effect.

Figure 6:
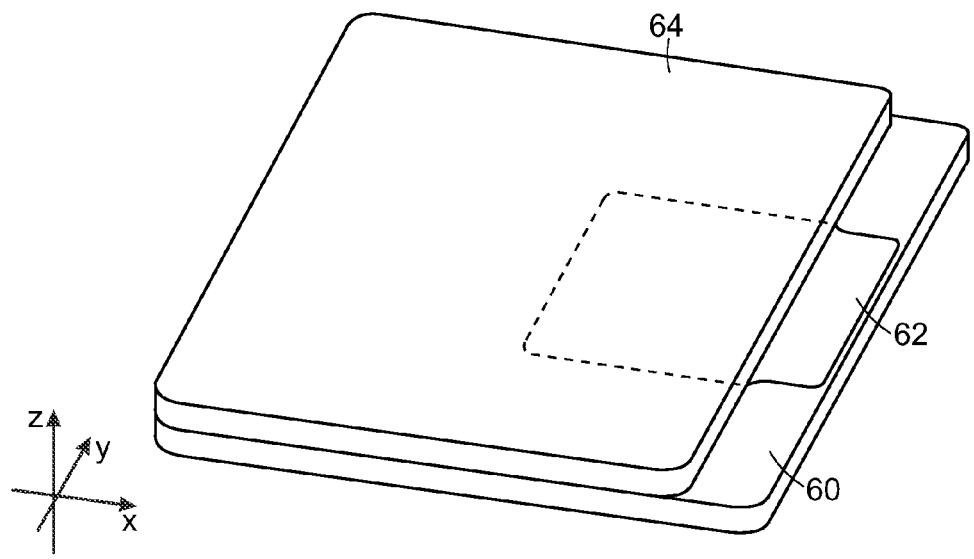
FIG. 6 shows an illustrative diagrammatic isometric view of a sensor system in accordance with an embodiment of the invention.

This cost advantage would be maintained even if the area of the SRM is greater than the area of the high impedance electrode. As shown in FIG. 6, a supporting substrate 60 on which a high impedance electrode 62 and signal receptive material 64 are applied may include much more supporting substrate and SRM than required; the SRM extends beyond the boundaries of the conductive electrode sensor. This configuration allows more control of adhesion of the electrode when the SRM is serving as the attachment adhesive as well as the signal receptive medium. It should be noted that if a typical hydrogel were so extended over the electrode, additional signals from the extra area covered by the hydrogel would cause some alteration in the position specificity of the ECG sensor. Thus, using a hydrogel extension to improve adhesion to the patient would have more than just a cost penalty.

Figure 7:
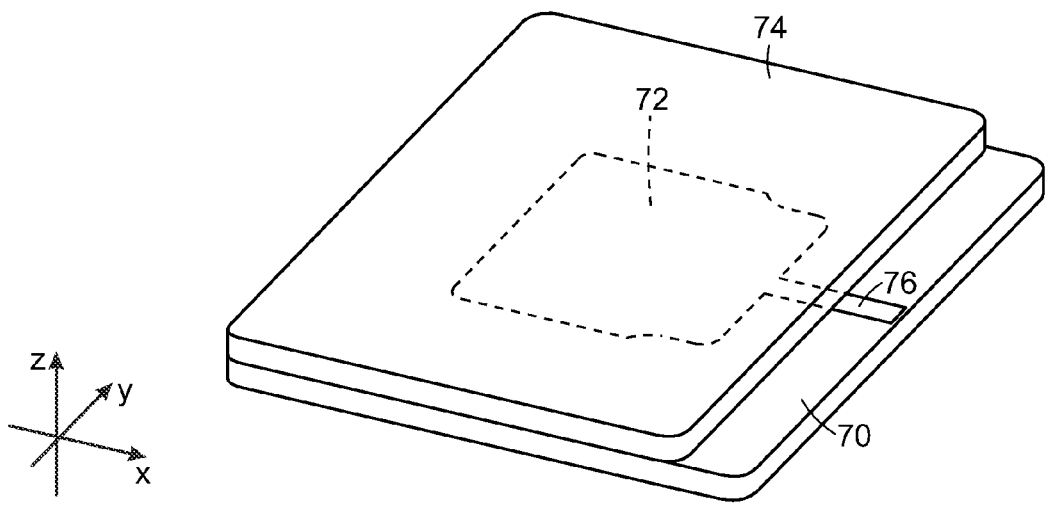
FIG. 7 shows an illustrative diagrammatic isometric view of a sensor system in accordance with another embodiment of the invention.

As shown in FIG. 7, the high impedance electrode sensor 72 may also be positioned well within the central region of the supporting substrate 70 and SRM 74 since any additional impedance of the lead 76 from the sensor 72 will not adversely impact reception of an output signal from the high impedance SRM material, provided that the ratio of the total area of the lead to the area of the electrode is small. If the ratio of areas $A_{lead}/A_{electrode}$ is larger than a critical ratio at which the lead itself may act as an effective electrode and pick up signals from areas away from the electrode, then a layer of insulating material or dielectric material of sufficient thickness may be disposed in alignment with the leads between the lead and the SRM to minimize or eliminate signal reception by the lead itself. The use of a high impedance SRM would not yield problems with signal fidelity.

Further the devices of FIGS. 6 and 7 would have the electrode and the surrounding skin better immobilized by the supporting substrate and the SRM. Thus inadvertent lifting of an edge of the electrode, or skin movement around the electrode, each of which may cause monitoring errors, may be minimized. An attempt to provide the same construction with a conventional ionically conductive hydrogel having a lower impedance adhesive, would permit signals generated from movements of the body around the electrode to be conducted in the X, Y plane of the hydrogel to the electrode.

An additional advantage of certain devices of the invention is that application of an array of electrodes on a continuous membrane to a patient, such as shown in FIGS. 4 and 5 using a continuous coating of high impedance SRM, would allow less adhesive thickness, and a less intrinsically tacky adhesive to be used. Adhesion to the patient would then be a function of total bond area, and would cause less discomfort to the patient upon removal.

Also, since such a system operates by capacitive coupling, the signal transmitted possesses low current characteristics, permitting the system to possibly be more desirable in electrical shunting conditions such as a defibrillation event. The high impedance electrode as well as the trace impedances may also serve to shield the patient and the medical personnel from excess current exposure.

Additionally, the possibility of multi-sensing electrodes (as shown in FIGS. 4 and 5), would allow a greater number of viewing angles that may aid signal detection and help a technician discern valid signals from external noise. This would also allow automated selection of which sensors are to be engaged.

Also, the ability to use higher impedance electrodes also provides that lower total metallic content may be employed, including the output leads to the ECG monitor and of the total electrode (plus SRM), lessening the requirement that the electrodes would have to be removed prior to other diagnostic tests such as X-ray, computer-aided tomography scans (CAT scans) and magnetic resonance imaging (MRI) analyses. Also, using non-metallic high impedance electrodes and output leads avoids many disposal problems concerning metals and metal salts.

An example of a sensor system of the invention that includes non-silver and silver chloride may be provided as follows. An ECG sensing electrode was constructed with the EXH-585 SRM material from the FLEXcon Company, Inc. of Spencer Mass. This adhesive operates via a non-ionic, capacitive coupling mechanism. The adhesive thickness was 25 microns, and applied to a 25 micron polyester film coated, on one side, with a conductive carbon coating (EXV-216 product from the FLEXcon Company) to a deposition of 25 microns, with an area of the conductively coated polyester not covered with the EXH-585 to allow an electrical contact to be made. The other end of the contact was to a GE Medical Systems model MAC 1200 ECG monitor. Three such pads were constructed and placed on a test subject, and an ECG reading was taken.

Figure 8A:
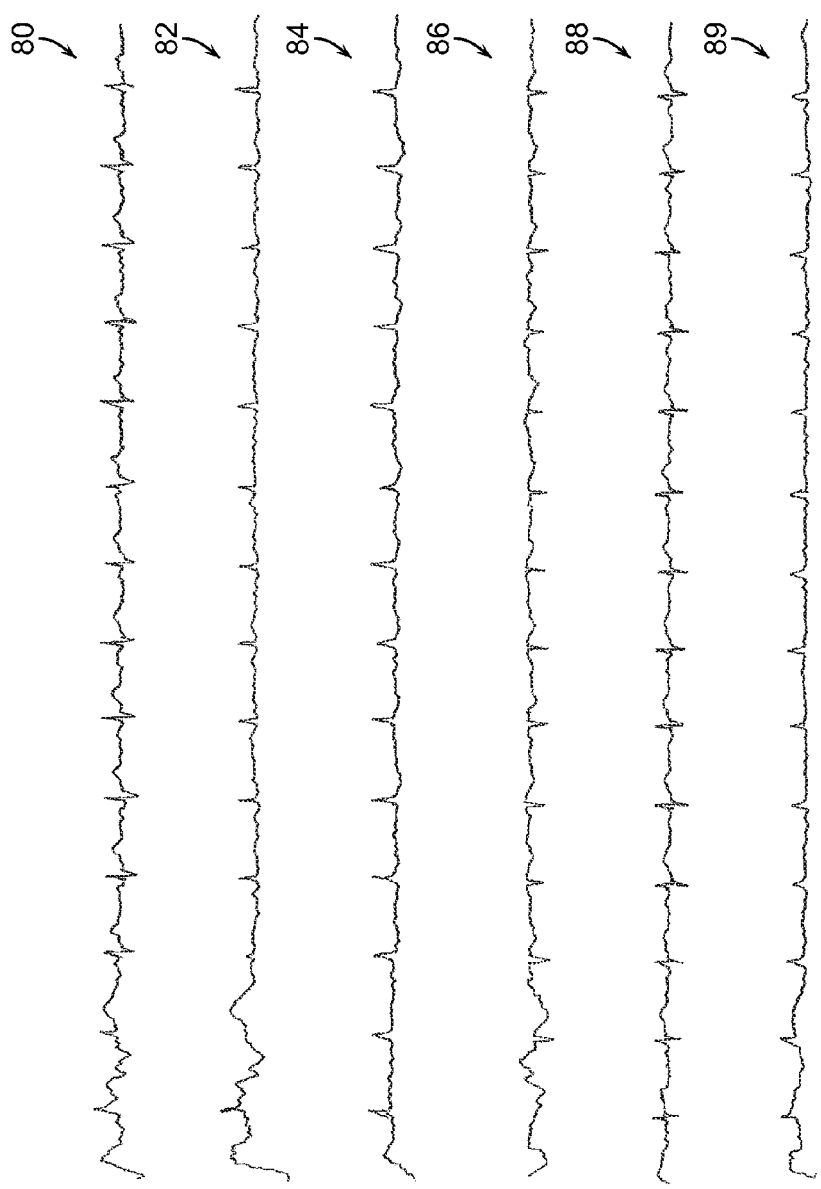
FIGS. 8A and 8B show illustrative graphical representations of ECG signals obtained from a system of the invention and a system of the prior art respectively.

FIG. 8A shows a sensor output that was provided by an ECG monitor representing certain portions of a composite signal, including for example, signals from the I, II, and III leads, as well as signals from the AVR, AVL and AVF leads. FIG. 8A shows the outputs of the I, II, III, AVR, AVL and AVF leads at 80, 82, 84, 86, 88 and 89 respectively for a subject using an SRM material as disclosed above in accordance with the invention.

Figure 8B:
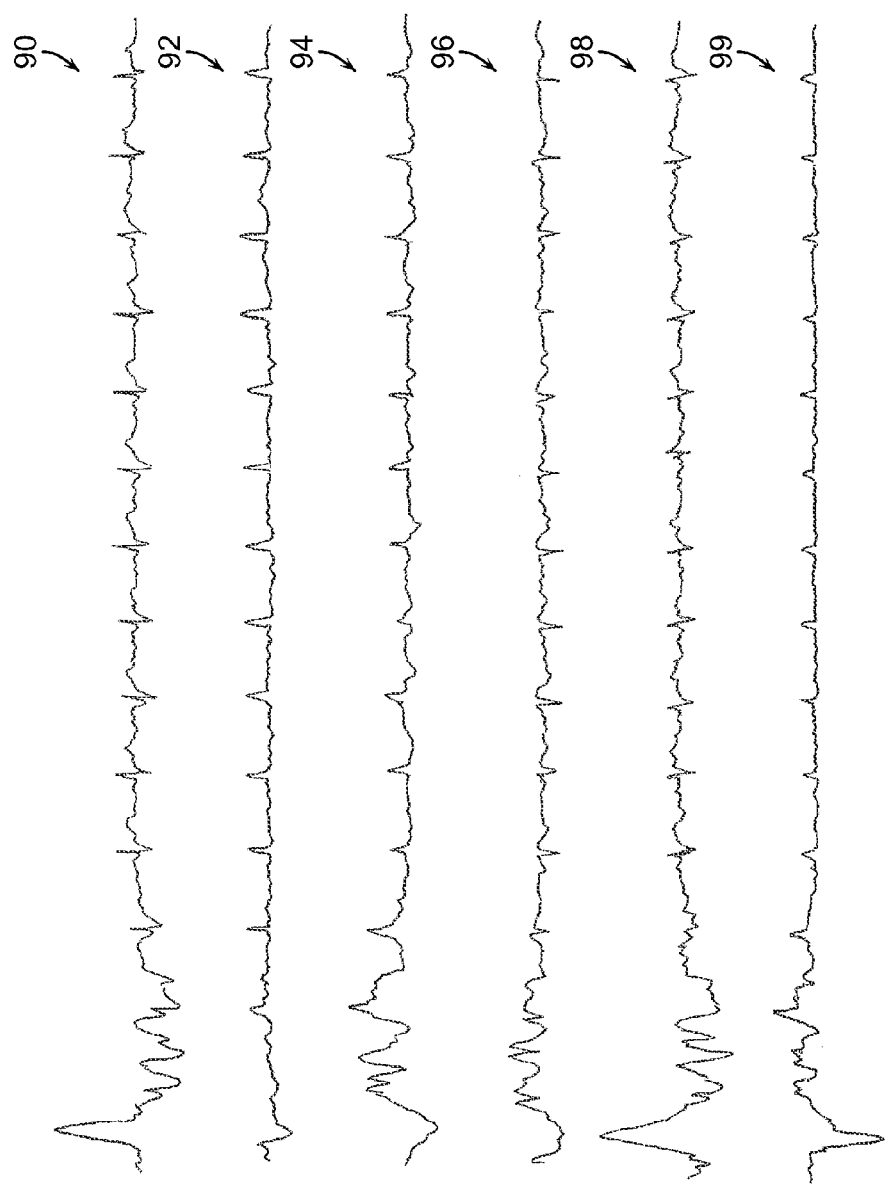

The same subject was retested with Kendall Q-Trace electrodes from Tyco Healthcare Retail Services AG Corporation of Switzerland using an ionically conductive hydrogel system on a polyester film with a silver/silver chloride coating over a conductive carbon coating, to receive the signal picked up by the hydrogel. The sensor outputs are provided to the ECG monitor, and signals from the I, II, and III leads, as well as signals from the AVR, AVL and AVF leads are shown at 90, 92, 94, 96, 98 and 99 respectively in FIG. 8B for the same subject using a hydrogel of the prior art. Comparisons of the two sets of ECG traces in FIGS. 8A and 8B show substantially the same signal fidelity.

As discussed above, another benefit of systems of the invention is the ability of the adhesive to cover in a continuous fashion two or more sensing electrodes. The SRM is not discreet with respect to a single electrode, but instead spans across, in the X, Y plane, several electrodes and still permits a strong, unique signal to be passed through the electrodes in the Z dimension. A series of tests were run to measure this effect.

Figure 9:
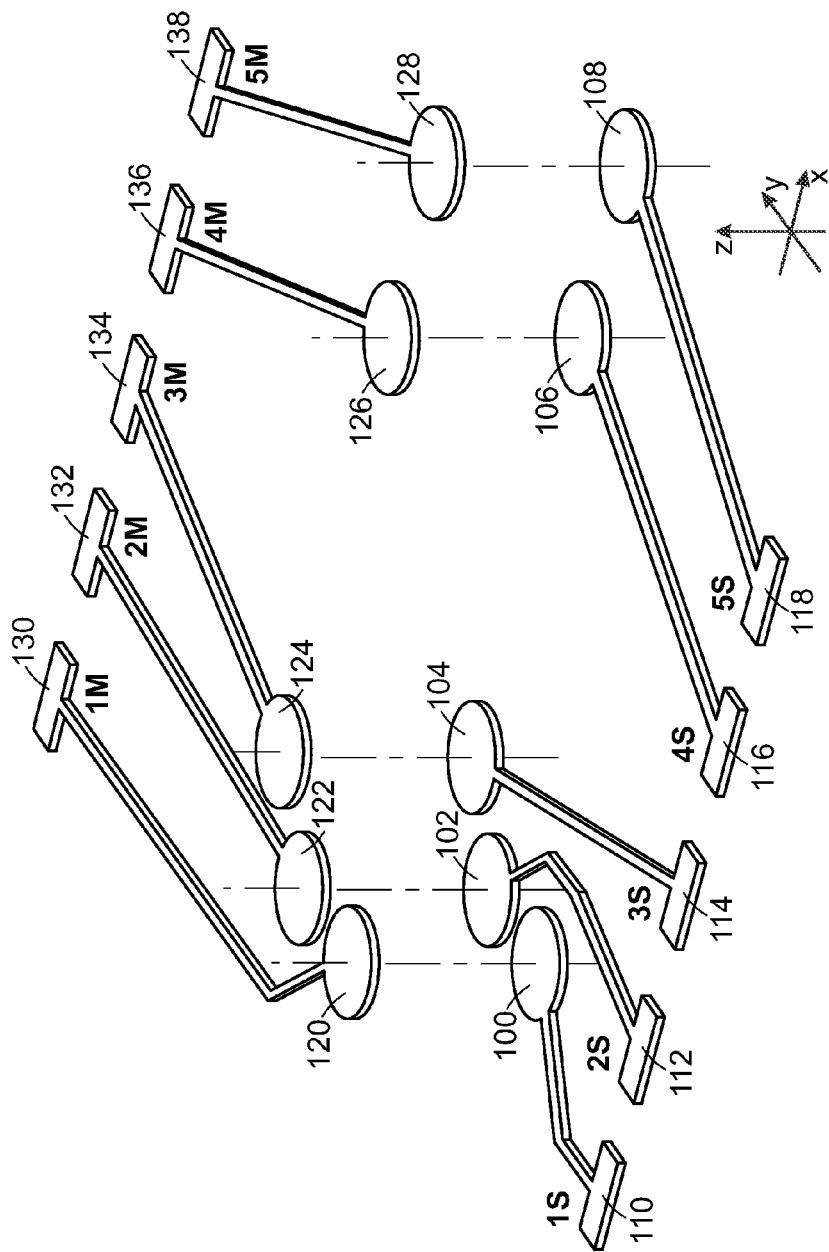
FIG. 9 shows an illustrative diagrammatic view of an electrode test fixture system employed for testing systems of the invention.

A test fixture of electrodes was provided as shown in FIG. 9. The test system also included a Spacelabs Model #514 Patient Monitor as sold by Spacelabs, Inc. of Chatsworth, Calif. as a common source of the test signals, as well as a GE Medical System Model # MAC 1200 as sold by General Electric of Schenectady, N.Y. for the signal receiver. As shown in FIG. 9, the test fixture of electrodes includes a first set of electrodes 100, 102, 104, 106 and 108 that are connected to the source via source high impedance connectors 110, 112, 114, 116 and 118 respectively, and a second set of electrodes 120, 122, 124, 126 and 128 that are connected to the monitor via high impedance monitor connectors 130, 132, 134, 136 and 138 respectively. The SRM material being tested is placed between the first set of electrodes and the second set of electrodes.

Separate signals were applied at source connections 2S (to electrode 102) and 3S (to electrode 104). Test samples were placed in direct physical contact with both the source and monitor connections so that the source signals could transmit through the test samples and be received at monitoring connections 2M (electrode 122) and 3M (electrode 124). The electrode pairs (100, 120), (102, 122), (104, 124), (106, 126) and (108, 128) comprised five electrode pairs that are designed to be placed at certain conventional locations on a human subject for measuring signals from a patient's heart. The sensor outputs are provided to an ECG monitor, and the monitor may provide a composite heart signal, and/or may provide discrete signals representing certain portions of a composite signal, including for example, the traditionally used ECG signals from the I, II, and III leads and from the AVR, AVL and AVF leads.

Five tests were conducted as follows. Test 1 provided a control in that the first and second sets of electrodes were on contact with one another. Test 2 provided a second control that employed a conventional hydrogel material located between the electrodes such that neighboring electrodes (e.g., 100 and 102) were provided with discrete regions of hydrogel. Test 3 provided a third control that employed an SRM as disclosed above that was located between the electrode pairs but was not common to more than one source or monitor electrode. Test 4 employed a large area of an SRM as discussed above that spanned across all electrode pairs. For example, the SRM between electrodes 102 and 122 was also between electrodes 104 and 124 in a continuous film. Test 5 employed a conventional hydrogel that spanned across all electrode pairs.

Figure 10A:
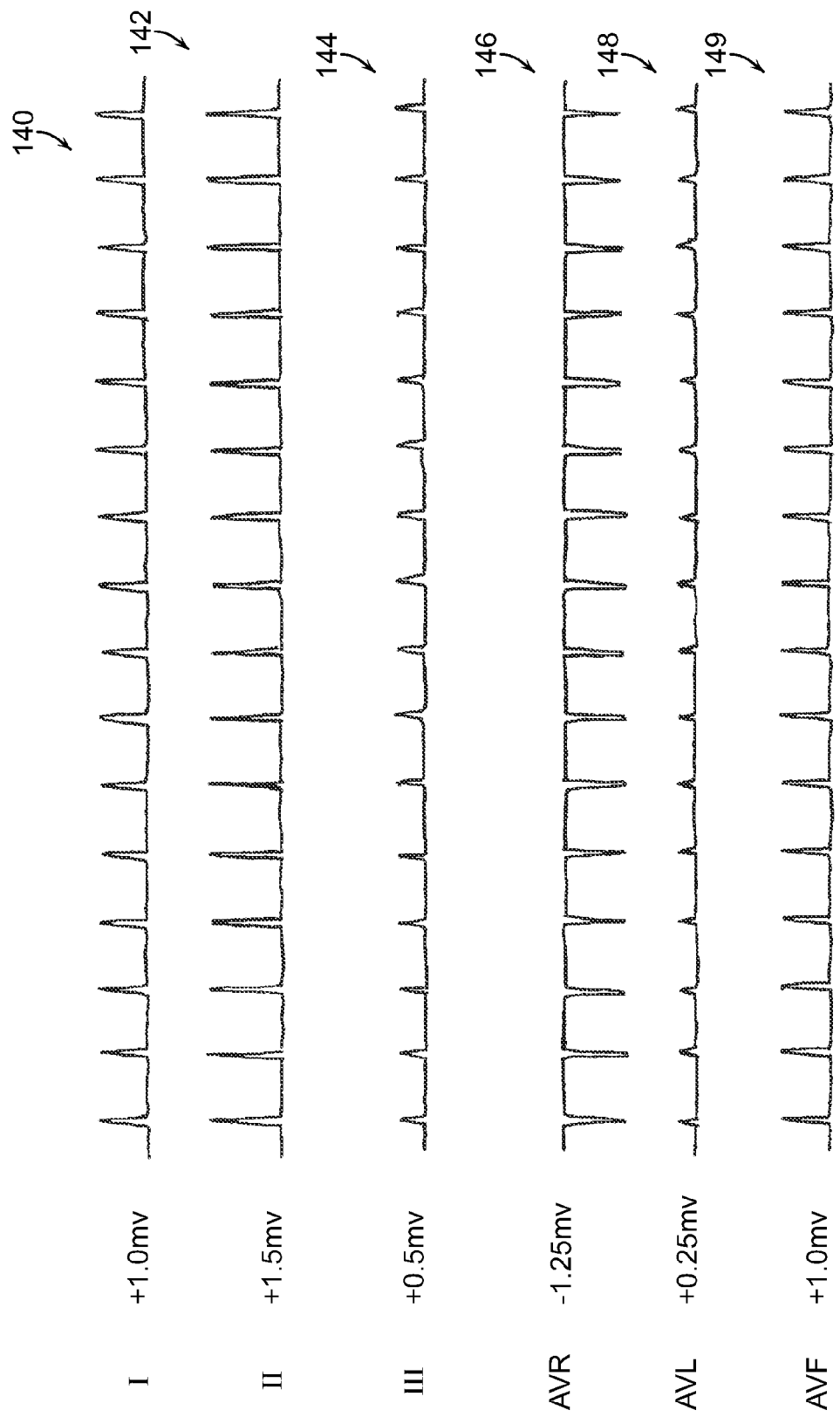
FIGS. 10A-10E show illustrative graphical representations of ECG I, II, II AVR, AVL and AVF signals obtained for purposes of testing multiple electrode systems in accordance with a further embodiment of the invention.
Figure 10B:
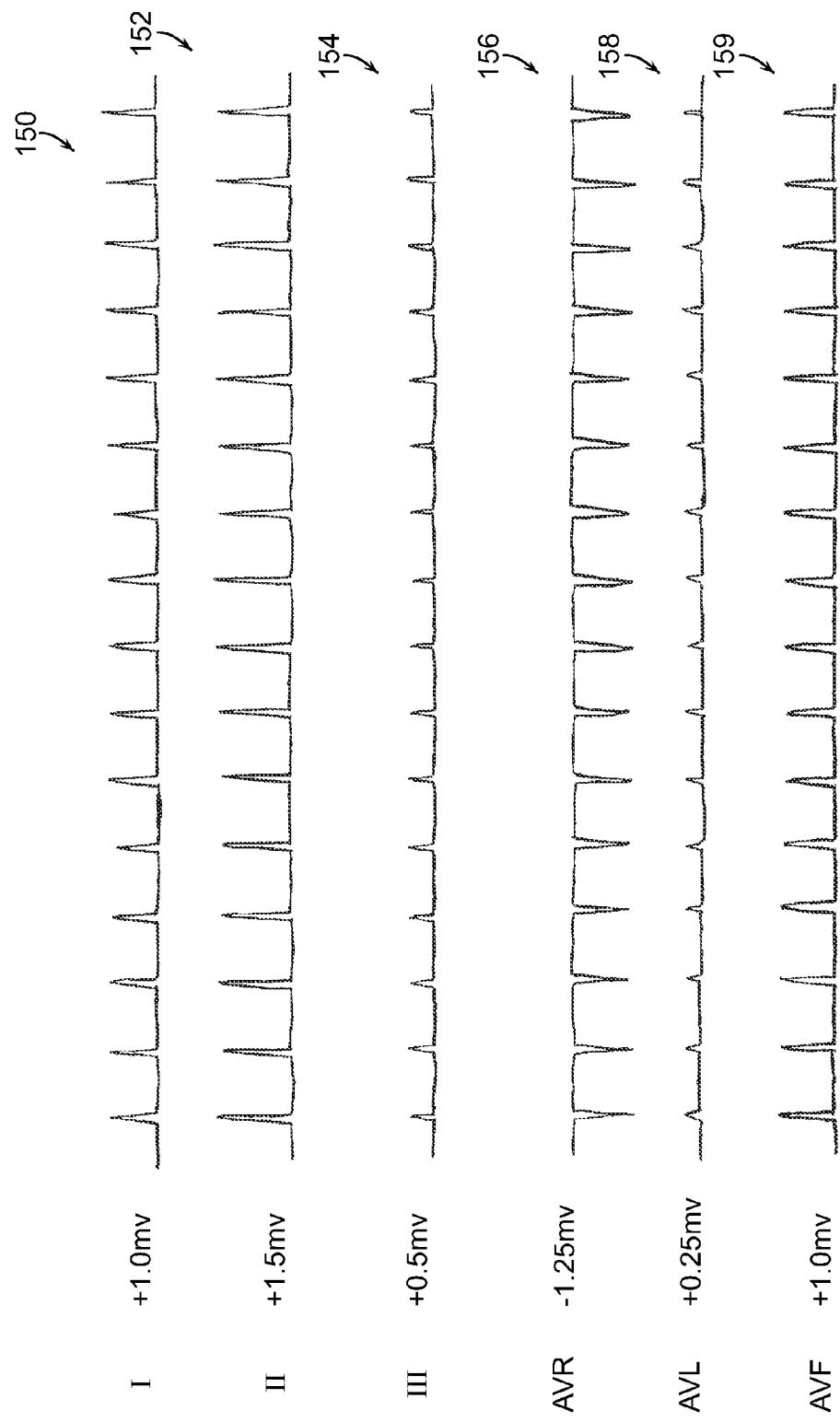
Figure 10C:
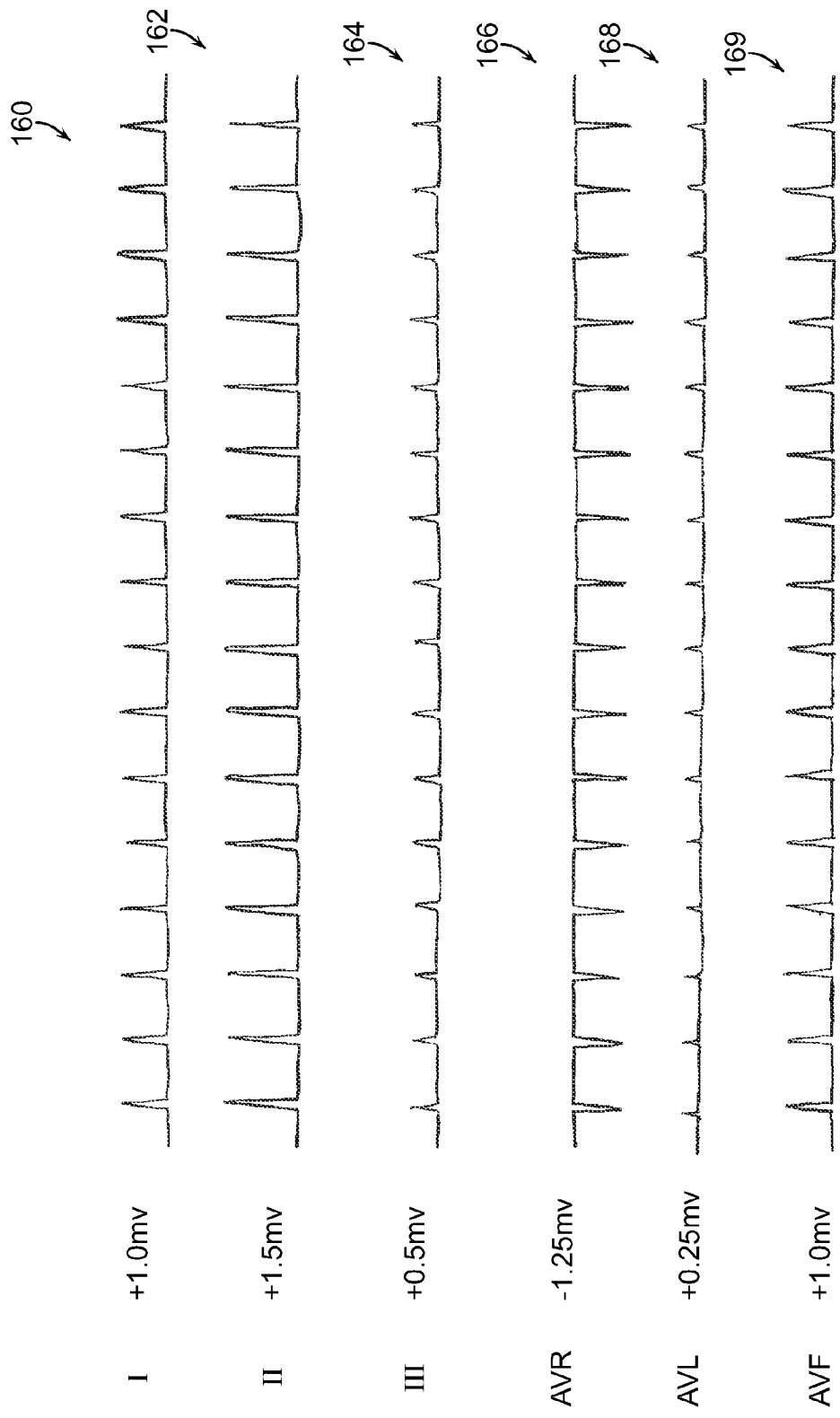
Figure 10D:
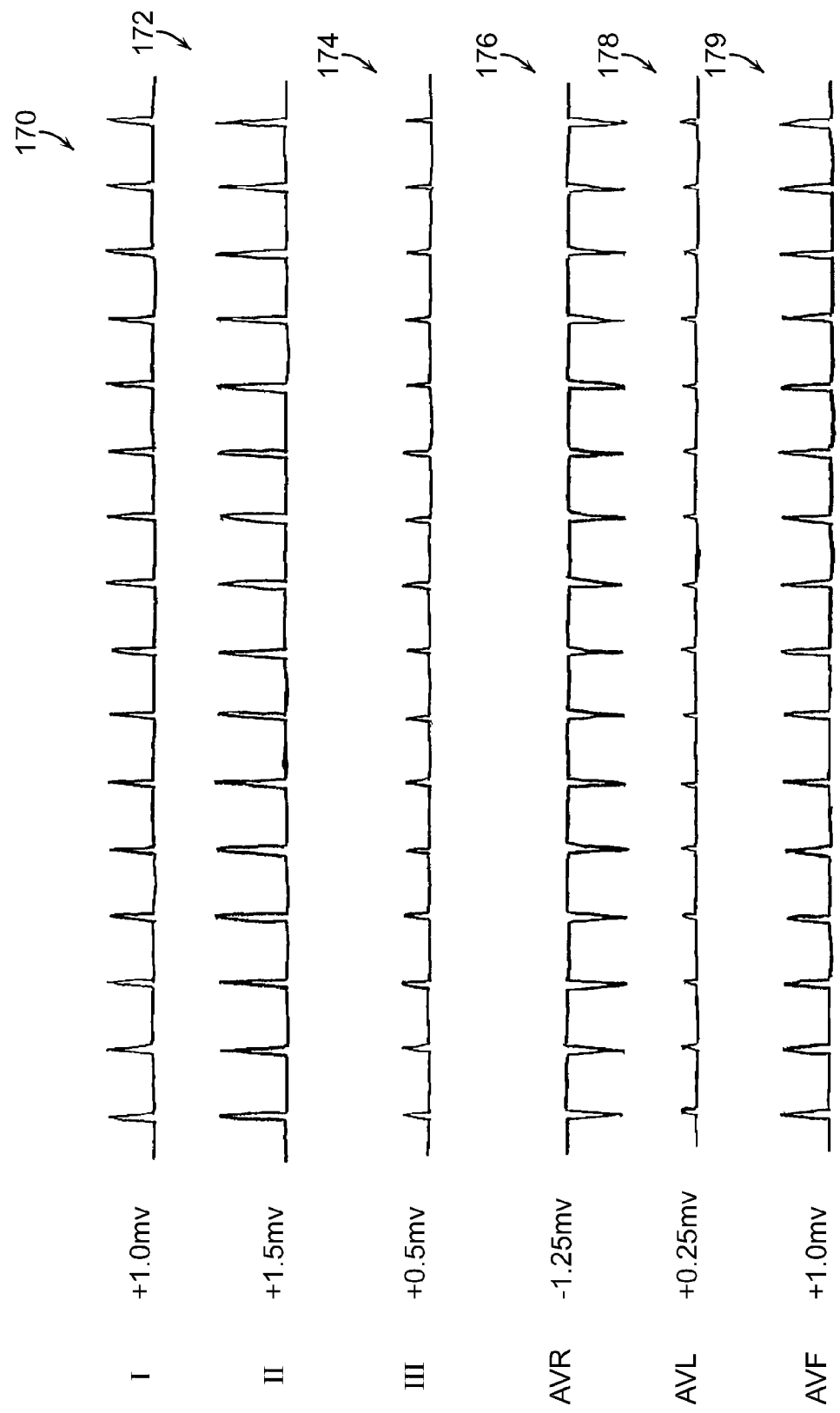
Figure 10E:
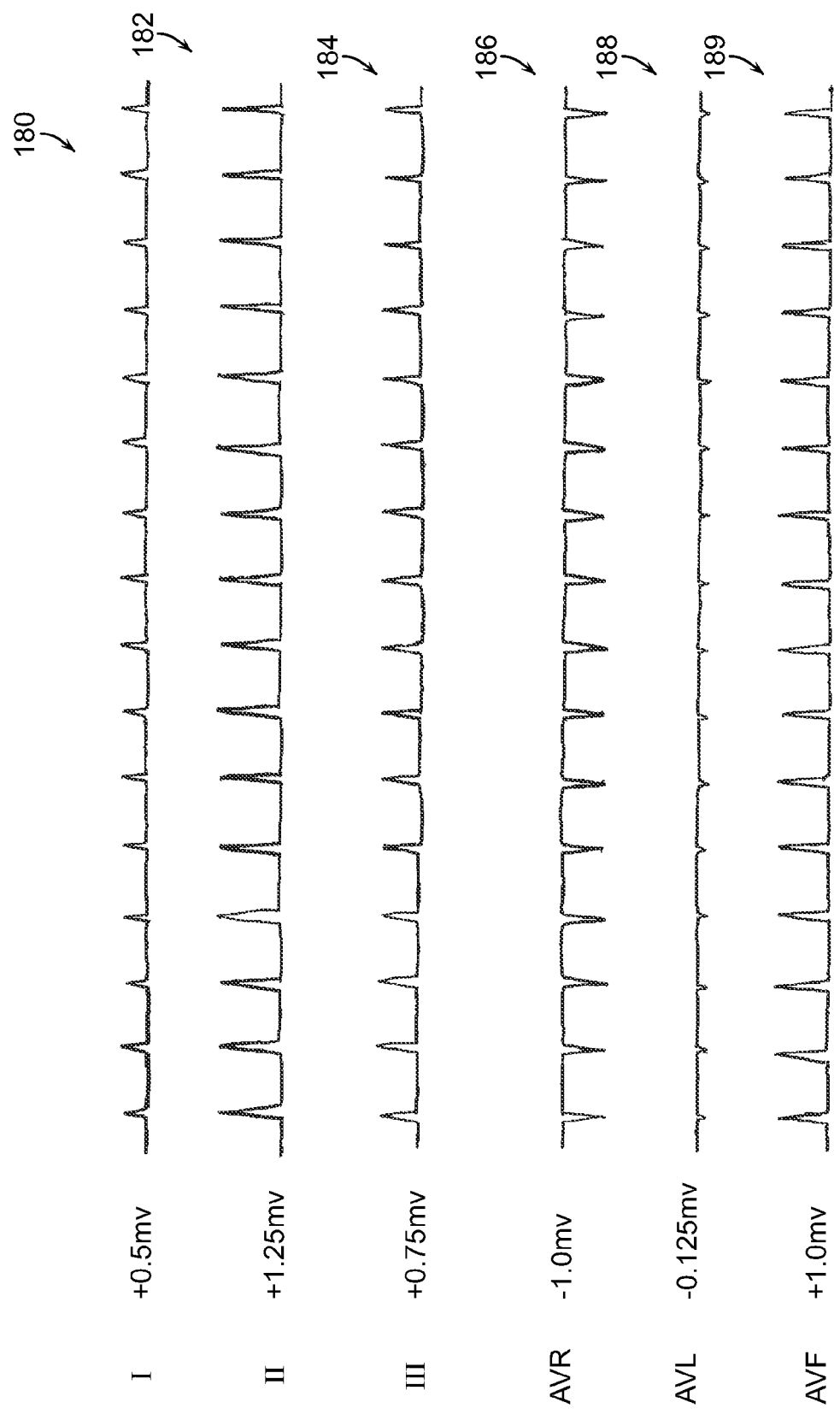

FIG. 10A shows the outputs of the I, II, III, AVR, AVL and AVF leads at 140, 142, 144, 146, 148 and 149 respectively for the control system (test 1) that includes no SRM material between each pair of electrodes. FIG. 10B shows the outputs of the I, II, III, AVR, AVL and AVF leads at 150, 152, 154, 156, 158 and 159 respectively for the control system (test 2) that includes a discrete portion of hydrogel material between each pair of electrodes. FIG. 10C shows the outputs of the I, II, III, AVR, AVL and AVF leads at 160, 162, 164, 166, 168 and 169 respectively for the control system (test 3) that includes a discrete portion of SRM material in accordance with the invention between each pair of electrodes. FIG. 10D shows the outputs of the I, II, III, AVR, AVL and AVF leads at 170, 172, 174, 176, 178 and 179 respectively for the system (test 4) that includes a continuous SRM material of the invention spanning across the area between each of the pairs of electrodes. FIG. 10E shows the outputs of the I, II, III, AVR, AVL and AVF leads at 180, 182, 184, 186, 188 and 189 respectively for the system (test 5) that includes a continuous hydrogel material of the prior art spanning across the area between each of the pairs of electrodes.

As may be seen in FIGS. 10A-10C, the standard ECG signals are very similar to one another for each of the control tests (tests 1-3) mentioned above. The system that employed a continuous SRM material of the invention (as shown in FIG. 10D) also provided standard I, II, III, AVR, AVL and AVF lead signals that were similar to those of FIGS. 10A-10C. The system of FIG. 10E, however, that employed a continuous hydrogel material of the prior art across each of the pairs of electrodes, produced lead I, lead III, lead AVR, and lead AVL signals of a much lower amplitude, and the polarity of the AVL signal was reversed. It is understood that this is because certain electrodes detected signals that were not immediately adjacent those electrodes, due at least in part to the fact that the common hydrogel material is conductive, not capacitive. Any effort to analyze such lead signals in an ECG system would result in incorrect (and possibly dangerously incorrect) readings. The system of FIG. 10D, however, functioned well even though a single continuous film of the SRM material was used for each of the pairs of electrodes.

This demonstrated another huge advantage of the SRM, with high internal impedance. Thus a multi-sensor composite, such as discussed above may be constructed with each sensor electrode covered by a continuous layer of an SRM without loss of point signal fidelity. Such a device would have numerous uses in medical and non-medical monitoring and/or diagnostic applications.

Figure 11:
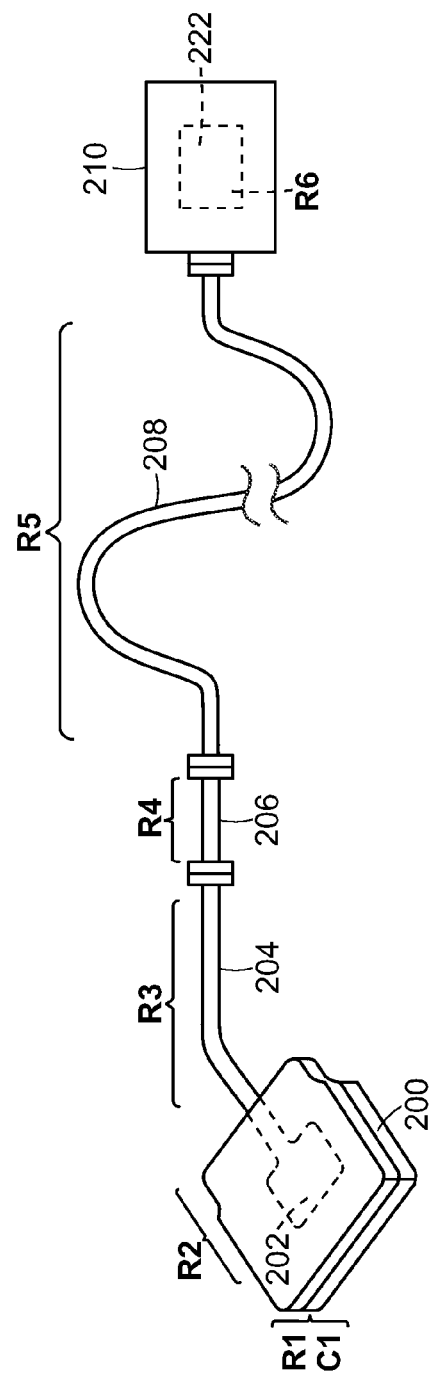
FIG. 11 shows an illustrative diagrammatic view of a system in accordance with a further embodiment of the invention.

As shown in FIG. 11, a system of the invention (including a high resistance adhesive material 200 and a conductor 202) may provide a sensor having high resistance ($R_1$) of between about 50,000 $\Omega$/sq-mil and about 500,000 $\Omega$/sq-mil (and preferably between about 150,000 $\Omega$/sq-mil and about 250, 000 Ω/sq-mil). The conductive electrode sensor may be formed of a high resistance material such as low cost conductive material such as aluminum, silver (very thin), silver chloride (very thin), tin, copper, or a conductive carbon coating such as the EXV-216 conductive polymer product sold by FLEXcon Company, Inc. of Spencer, Mass., or a conductive polymer such as the CLEVIOS conductive polymer products sold by H.C. Starck GmbH. of Germany, and may have a surface resistance of between about 30 Ω/sq-mil and about 3,000 Ω/sq-mil (and preferably between about 100 Ω/sq-mil and about 1,500 Ω/sq-mil).

Additional resistance provided by the connecting electronics may be significantly higher than conventionally employed. For example, a lead 204 extending from the conductor 202 (including an optional further lead extension 206 coupled thereto) extending from the conductor 202 may be formed of a low cost high resistance material such as aluminum, silver (very thin), silver chloride (very thin), tin, copper, or a conductive carbon coating such as discussed above.

A flexible high impedance signal transport conductor 208 coupled thereto and to a monitor system 210 may be formed of a high resistance material such as conductive carbon, and may have a resistance of between about 0.012 Ω/sq-mil and about 106 Ω/sq-mil (and preferably between about 0.1 Ω/sq-mil and about 20 Ω/sq-mil). Such a cable may provide improved flexibility due to the relaxation of a need to have the cable be highly conductive.

The high impedance electrode 202 is a signal receptive patch that may consist of an Ag/AgCl, Cu, Sn, conductive carbon coating, or a signal conductor material with similar signal conducting properties. Leads 204 and 206 may consist of high impedance signal conducting traces that may consist of conductive carbon, conductive graphite, or a similar high impedance signal conductor. The resistance R5 represents the wire transmitter that transmits the signal to the cardiac output ECG machine.

Figure 12:
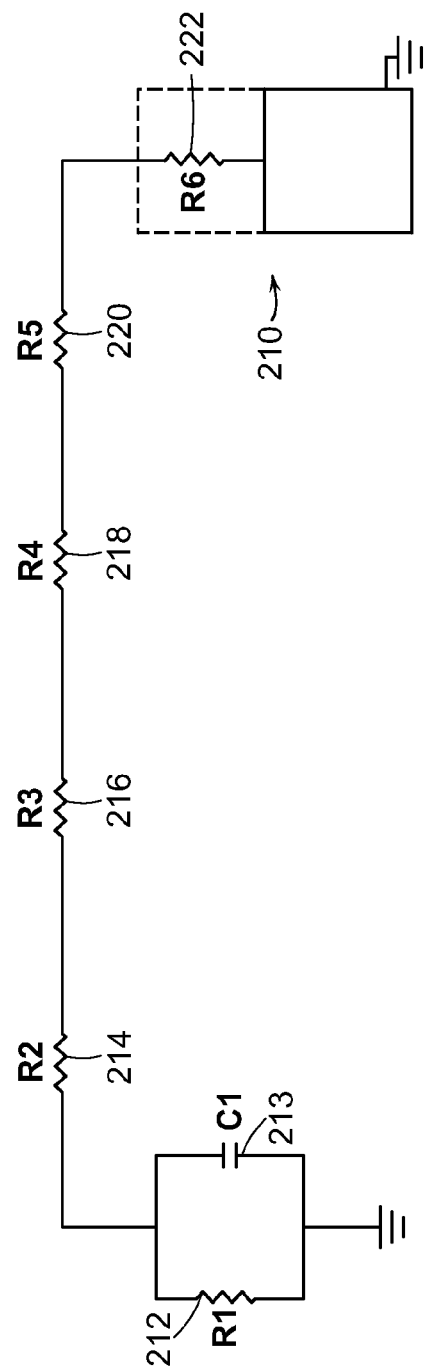
FIG. 12 shows a diagrammatic view of the electrical components of the system of FIG. 11.

FIG. 12 contains an electrical representation of the constructed elements in FIG. 11 in which the electrical diagram symbolizes the methods of signal transmission. Adhesive 200 from FIG. 11 representing the adhesive medical electrode undergoes a polarization when subjected to a low frequency biomedical (e.g., AC) signal such as an ECG signal. For this reason, the signal transmission behaves in a similar manner to a charging capacitor. At a low frequency, a capacitor acts like an open circuit, blocking any DC (or low frequency) current. High impedance conductor 212 (R1) in parallel with capacitor 213 (C1) quantifies the adhesive's low frequency impedance. The capacitive polarization transmits the low frequency signal without significant current transmission. The resistance value R2 of FIG. 11 is shown at 214. Resistors R3, R5, and R5 (of FIG. 11) are shown at 216, 128 and 220, and represent the impedance of the signal receptive conductive patch, the signal transmitting conductive traces, and the conductive wire leading to the ECG output. The combined impedance of all the elements in FIG. 511 excluding R6 (shown at 222) should be at least 20KΩ. Resistor 222 (R6) in FIG. 12 represents the input impedance of the cardiac output ECG machine. This impedance may be as large as 100 MΩ as in the GE MAC 1200 ECG monitor.

The input impedance of the monitor affects signal transmission because of the functional characteristics of a voltage divider. In signal transmission, a signal's amplitude is divided among many series resistance elements proportionally. The input impedance of the ECG machine is still several magnitudes larger than the combined series impedance of elements R1-R5 in FIG. 12. The higher impedance ensures that the majority of the signal amplitude is accurately transmitted to the ECG monitor as represented in the formula $V_{out}ECG = V_{in}$ medical electrode $[R6/(R6+R5+R4+R3+R2)]$. In an example where the $V_{in}$ Medical Electrode signal amplitude is 100 mV, R6=100MΩ, R2-R5=20 kΩ, $V_{out}ECG$ would equal 99.9 mV of the signal transmitted.

Those skilled in the art will appreciate that numerous modifications and variations nay be made to the above disclosed embodiments without departing from the spirit and scope of the invention.

What is claimed is:

1. A biomedical sensor system comprising a high impedance conductive electrode having an electrode impedance of at least about 20 kΩ/sq-mil, and a dielectric material on a first side of said electrode for receiving a discharge of an electrical signal from the dielectric material responsive to the presence of a time varying signal adjacent a second side of said dielectric material that is opposite the first side.

2. The biomedical sensor system as claimed in claim 1, wherein said dielectric material is an adhesive.

3. The biomedical sensor system as claimed in claim 1, wherein said dielectric material includes multiple electrodes on the first side thereof.

4. The biomedical sensor system as claimed in claim 1, wherein said conductive electrode includes a conductive polymer.

5. The biomedical sensor system as claimed in claim 1, wherein said conductive electrode includes any of aluminum, silver, silver chloride, or a conductive graphite.

6. The biomedical sensor system as claimed in claim 1, wherein said conductive electrode is printed onto a substrate.

7. The biomedical sensor system as claimed in claim 1, wherein said conductive electrode includes a conductive carbon coating.

8. The biomedical sensor system as claimed in claim 1, wherein said biomedical sensor system include a monitor system that is coupled to the conductive electrode via a conductive path, and wherein a resistance of the conductive path between the conductive electrode and the monitor system is at least about 1 Ω/sq-mil.

9. The biomedical sensor system as claimed in claim 1, wherein the high impedance conductive electrode and the dielectric material have a combined thickness of less than about 250 microns.

10. A biomedical sensor system comprising a first conductive electrode and a second conductive electrode that is adjacent the first conductive electrode, said first and second conductive electrodes being provided in contact with an anisotropic signal receptive material that is contiguous with both the first conductive electrode and the second conductive electrode and wherein the contiguous receptive material provides that a biomedical signal from a first side of the signal receptive material is detectable by the first conductive electrode that opposes the biomedical signal but is not detectable by the second conductive electrode that does not oppose the biomedical signal irrespective of the thickness of the signal receptive material.

11. The biomedical sensor system as claimed in claim 10, wherein said system further includes an array of conductive electrodes in contact with the signal receptive material such that the signal receptive material is contiguous with each of a plurality of electrodes in the array of conductive electrodes.

12. The biomedical sensor system as claimed in claim 10, wherein said signal receptive material is an adhesive that exhibits dielectric dispersion.

13. The biomedical sensor system as claimed in claim 10, wherein each of said first and second conductive electrodes has a resistance of at least about 50 kΩ/sq.-mil.

14. The biomedical sensor system as claimed in claim 10, wherein said system further includes an ECG harness of conductive electrodes in contact with the signal receptive material such that the signal receptive material is contiguous with each of a plurality of electrodes in the ECG harness of conductive electrodes.

15. A biomedical sensor system comprising a flexible structural support layer having a first length, a first width, and a first thickness, an electrically conductive layer having a second length, a second width, and a second thickness, and a dielectric material layer having a third length, a third width, and a third thickness, said dielectric material layer including a dielectric material that changes its dielectric properties responsive to the presence of a time varying signal, wherein at least one of the second length and the second width is less than a respective one of the third length and the third width, wherein the dielectric material is contiguous, and provides that a first biomedical signal from a first side of the contiguous dielectric material that opposes the electrically conductive layer is detectable by the electrically conductive layer while another biomedical signal from the first side of the contiguous dielectric material that does not oppose the electrically conductive layer is not detectable by the electrically conductive layer and wherein the third thickness is between about 5 microns and about 200 microns.

16. The biomedical sensor system as claimed in claim 15, wherein at least one of the second length and the second width is less than a respective one of the first length and the first width.

17. The biomedical sensor system as claimed in claim 15, wherein the sum of the first, second and third thicknesses is less than about 250 microns.

\* \* \* \* \*